United States Patent [19]

Uddenberg

[11] Patent Number: 4,512,347
[45] Date of Patent: Apr. 23, 1985

[54] OBSTETRIC SUCTION DEVICE

[75] Inventor: Göran O. Uddenberg, Marstrand, Sweden

[73] Assignee: AB Vacuum-Extractor, Göteborg, Sweden

[21] Appl. No.: 452,817

[22] Filed: Dec. 23, 1982

[30] Foreign Application Priority Data

Dec. 28, 1981 [SE] Sweden .............................. 8107786

[51] Int. Cl.³ ............................................ A61B 17/42
[52] U.S. Cl. ................................... 128/352; 128/361
[58] Field of Search ............... 128/352, 361, 323, 324

[56] References Cited

U.S. PATENT DOCUMENTS

| 655,509 | 8/1900 | Olson | 128/352 |
| 2,702,038 | 2/1955 | Uddenberg et al. | 128/361 |

FOREIGN PATENT DOCUMENTS

| 2006222 | 8/1971 | Fed. Rep. of Germany | 128/352 |
| 215409 | 7/1968 | U.S.S.R. | 128/352 |

Primary Examiner—Michael H. Thaler
Attorney, Agent, or Firm—Holman & Stern

[57] ABSTRACT

An obstetric suction device for vacuum extractors and consisting of a suction device (11) with a connecting mechanism (15) for a suction hose and a traction device (16) attachable to the cup. The object of the invention is to provide a suction cup which does not give right to any pressure force component, regardless of how the tractive force is applied to the cup. This has been attained by making the traction device (16) in the form of a two-point pulling device which is attachable to two attachments (18) disposed in proximity of the opening (12) of the cup and diametrically opposite to one another.

4 Claims, 4 Drawing Figures

OBSTETRIC SUCTION DEVICE

The present invention relates to obstetric suction devices for vacuum extractors and of the kind comprising a suction cup of a rigid material, means for connecting a suction hose to said cup, and a traction device attachable to said cup.

BACKGROUND OF THE INVENTION

There are mainly two categories of obstetric suction devices, those made from an elastically yielding material, such as rubber, and those made from a rigid material, such as metal, e.g. stainless steel. There is a difference of opinion about the advantages of one category or the other, but extensive clinical use has shown that injuries are more frequent when using a soft suction cup than when using a hard one. The injuries which may occur in connection with the use of these suction devices are mainly contusions and are of a considerably less serious type than those usually occuring when deliveries are performed with the aid of obstetric forceps.

During the delivery process the head and body of the fetus are adjusted in the various sections of the delivery canal in such a manner, that the fetus may pass with the least possible resistance. To obtain this adjustment in the case of a fully dilated cervix it may be necessary, in the second phase of the delivery, to apply the suction cup over the rear fontanelle of the fetus, so that the center of the cup is directed towards sutura sagitalis. Previously known suction cups of the kind mentioned above are provided with a pulling handle attached to the central portion of the cup. Due to the central location of the handle on top of the suction cup, the tractive force will even be distributed when the handle is pulled at right angles to the suction surface, whereas a pulling force applied at an angle to the suction surface either will cause the suction cup to be pulled loose or cause a portion of the edge of the suction opening to apply a pressure against the head of the child. This pressure may be large enough to cause severe pressure marks.

Since the application of the suction cup has to be made within the uterus, it is important that the suction cup does not occupy a large space. Above all it is important that the cup does not have any projecting portions which may cause damages or inconvenience.

THE OBJECT AND MAIN CHARACTERISTICS OF THE INVENTION

The object of the present invention is to provide a suction cup which—independently of the direction of the pulling force to which the suction cup is subjected—will not be pulled loose or give rise to pressure forces, but will subject the suction surfaces to tractive forces only. Another object of the invention is to provide a suction cup which, on the surface facing the uterus, has practically no projecting parts which could cause damages on the child or the mother. These objects have been attained by making the traction device in the form of a two-point pulling device attachable to two attachments disposed diametrically opposite one another in close proximity to the opening of the cup.

DESCRIPTION OF AN EMBODIMENT

Figure 1:
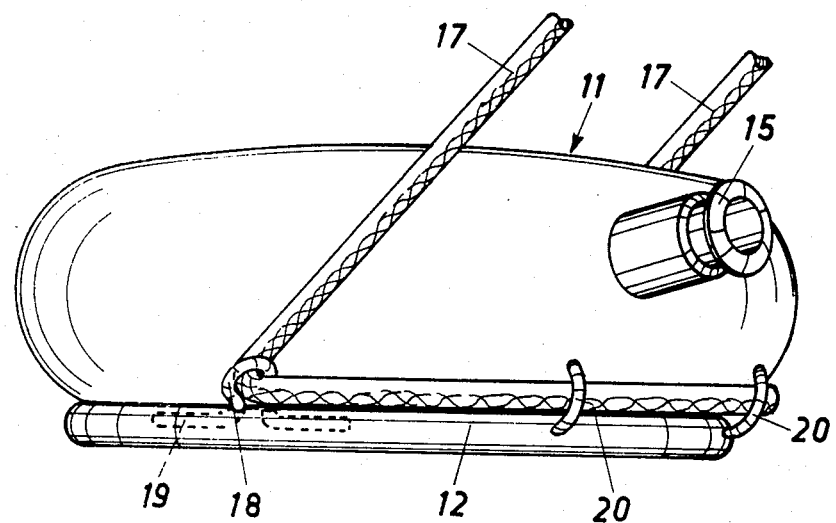
FIG. 1 is a side view of a suction device according to the invention.
Figure 2:
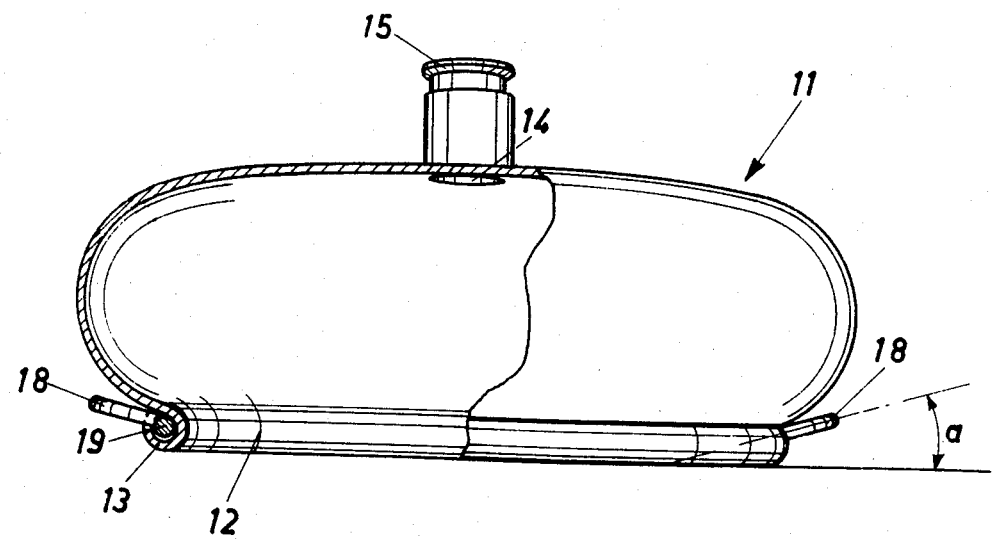
FIG. 2 shows a slightly modified suction device partly in section.
Figure 3:
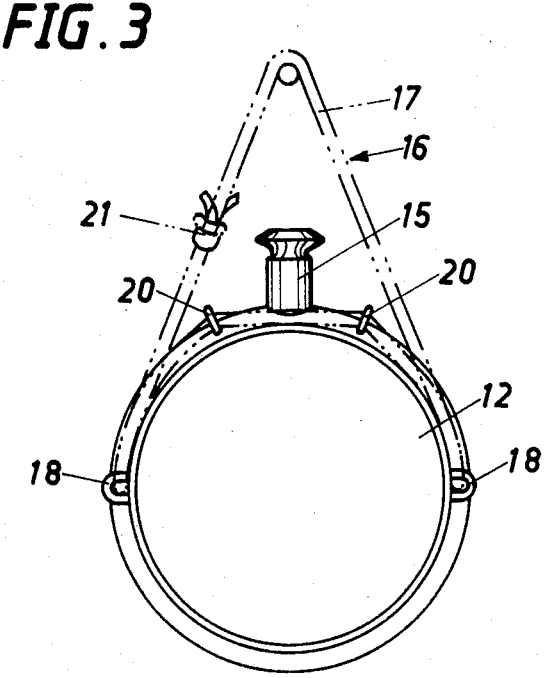
FIG. 3 is a view to a smaller scale from the underside of the suction device according to FIG. 1.

The obstetric suction device consists of a suction cup 11 with a comparatively small height in relation to its circumference and having a large opening 12 which is surrounded by a rolled-around edge 13. The cup has a softly rounded, circular shape, and in the side-wall of the cup there is provided an evacuation opening 14 for a connecting piece 15 which is intended for the connection thereto of a hose leading to a vacuum device (not shown) which may be either of a manually operated type or a motor-driven type. In the embodiment shown in FIG. 2 the connecting piece 15 with evacuation opening 14 is arranged on the upper side of the cup.

To the suction cup there is connected a traction device 16 which in the embodiment shown is in the form of a sterilizable string 17 or ribbon which is connected to the suction cup 11 by means of two loop-shaped attachments 18 disposed diametrically opposite one another and in close proximity to the opening 12 of the cup. The loop-shaped attachments 18 are made with extended laterally directed legs 19 which are located in the rolled edge 13 and soldered to the cup. Preferably, the attachment loops 18 form an angle "a" of about 20°-30° to the plane of the opening 12.

Since a soft string or ribbon 17 is the most convenient that can be used in this connection and since it is not desirable to have a knot in connection with the suction cup, the string 17 is placed around approximately half the circumference of the cup and fixed in this position by means of a number of guiding loops 20. In this way, a knot 21 which connects the ends of the string 17 may be placed at a distance from the suction cup in such a manner that the knot will not be of inconvenience.

Figure 4:
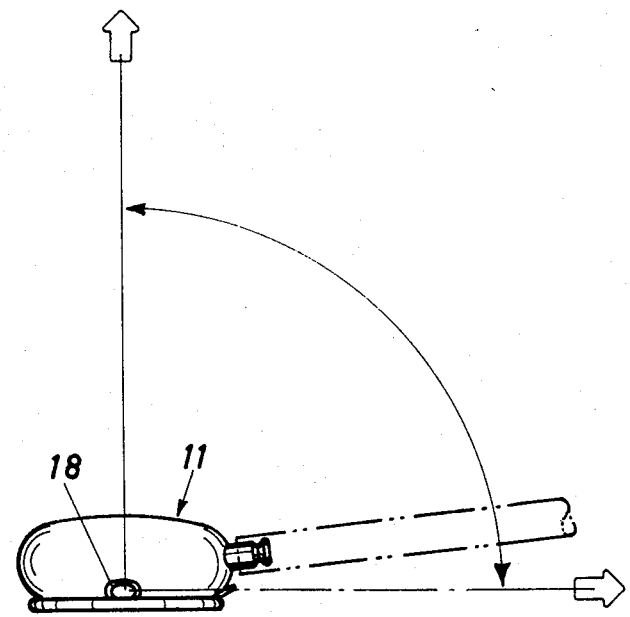
FIG. 4 is a side-view of the suction device according to the invention and illustrating the limits of the pulling angle of the traction device.

Due to the fact that the attachment loops 18 are placed as close as possible to the opening 12 of the cup, in view of the attachment and position of the loops, and in such a manner that the loops project out from the cup as little as possible, the stresses acting upon the suction cup will only be in the form of tractive forces over an angle of about 90°, see FIG. 4, without the occurence of any bending forces which may cause the suction cup to turn over and be pulled loose, and without the occurence of any pressure forces.

I claim:

1. An obstetric suction device for vacuum extractors comprising a suction cup of a rigid material having a suction mouth, a connection piece for connecting a suction hose to said suction cup, a traction device attachable to said cup, the traction device being in the form of a two-point pulling device attachable to two attachments disposed diametrically opposite one another in close proximity to the suction mouth of the cup in such a manner that the attachments are in the form of loops which are oblique with respect to the plane of the suction mouth and the traction device is in the form of a string, ribbon or similar soft and flexible member which extends from said attachment loops around approximately half the circumference of the cup and held in this position by means of guiding means.

2. The suction device as claimed in claim 1, wherein the attachments are in the form of loops arranged at an angle of 20°-30° to the plane of the suction mouth.

3. The suction device as claimed in claim 1 wherein the loops are transverse to the longitudinal axis of the connection piece.

4. The suction device according to claim 4 wherein the edge of the suction cup is rolled around outwardly, and extended leg portions of the attachment loops are secured therein.

* * * * *